United States Patent
Sato et al.

(10) Patent No.: US 10,797,433 B2
(45) Date of Patent: Oct. 6, 2020

(54) TERMINAL PROTECTION PARTS

(71) Applicant: SHARP KABUSHIKI KAISHA, Sakai, Osaka (JP)

(72) Inventors: Tadahiko Sato, Sakai (JP); Yan Qian, Sakai (JP)

(73) Assignee: SHARP KABUSHIKI KAISHA, Sakai, Osaka (JP)

( * ) Notice: Subject to any disclaimer, the term of this patent is extended or adjusted under 35 U.S.C. 154(b) by 0 days.

(21) Appl. No.: 16/297,397

(22) Filed: Mar. 8, 2019

(65) Prior Publication Data

US 2019/0305474 A1 Oct. 3, 2019

(30) Foreign Application Priority Data

Mar. 30, 2018 (JP) ................. 2018-069144

(51) Int. Cl.
*H01R 13/52* (2006.01)
*H01R 13/627* (2006.01)
*H01R 13/62* (2006.01)

(52) U.S. Cl.
CPC ..... *H01R 13/5213* (2013.01); *H01R 13/6205* (2013.01); *H01R 13/6278* (2013.01)

(58) Field of Classification Search
CPC ............ H01R 13/447; H01R 13/4538; H01R 13/5213; H01R 13/6278; H01R 13/5045
USPC .................... 439/141, 138, 142, 39
See application file for complete search history.

(56) References Cited

U.S. PATENT DOCUMENTS

| | | | | |
|---|---|---|---|---|
| 4,228,317 A | * | 10/1980 | Cziment | H01R 13/447 174/67 |
| 5,730,622 A | * | 3/1998 | Olson | H01R 13/6474 439/575 |
| 5,852,394 A | * | 12/1998 | Watanabe | H02J 7/025 336/66 |
| 6,198,046 B1 | * | 3/2001 | Moodie | H01R 13/6395 174/67 |
| 6,890,188 B1 | * | 5/2005 | Le | G06F 13/385 439/76.1 |
| 8,337,222 B2 | * | 12/2012 | Hung | H01R 13/447 439/138 |
| 9,025,320 B2 | * | 5/2015 | Neukam | G06F 1/181 361/679.02 |
| 2004/0067667 A1 | * | 4/2004 | Kuroki | H01R 13/4532 439/138 |
| 2007/0117428 A1 | * | 5/2007 | Mossner | H01R 13/447 439/138 |

(Continued)

FOREIGN PATENT DOCUMENTS

| | | |
|---|---|---|
| CN | 101841097 A | 9/2010 |
| CN | 206728355 U | 12/2017 |
| JP | 2013-105048 A | 5/2013 |

*Primary Examiner* — Abdullah A Riyami
*Assistant Examiner* — Marcus E Harcum
(74) *Attorney, Agent, or Firm* — ScienBiziP, P.C.

(57) ABSTRACT

A connector unit includes a connector and a plurality of connector cap parts that are rotatably attached to a side wall of the connector. The connector cap parts each have a first space for receiving an end portion of the connector. The connector cap parts rotate toward the connector and are joined together to form a connector cap so that the first spaces communicate with each other to form a second space and that the end portion is placed in the second space.

4 Claims, 11 Drawing Sheets

(56) References Cited

U.S. PATENT DOCUMENTS

| | | | |
|---|---|---|---|
| 2013/0017696 A1* | 1/2013 | Alvarez Rivera | H01R 13/447 439/142 |
| 2015/0118874 A1* | 4/2015 | Watanabe | H01R 13/64 439/138 |
| 2016/0104962 A1* | 4/2016 | Lee | H01R 13/4536 439/138 |
| 2016/0111806 A1* | 4/2016 | Kloosterboer | H01R 13/447 439/38 |
| 2016/0240954 A1* | 8/2016 | Grudzewski | H01R 13/582 |
| 2017/0062969 A1* | 3/2017 | Kida | H01R 13/5219 |
| 2018/0183191 A1* | 6/2018 | Endo | H01R 13/6596 |
| 2018/0212360 A1* | 7/2018 | Motohashi | H01R 13/447 |

* cited by examiner

TERMINAL PROTECTION PARTS

BACKGROUND

1. Field

The present disclosure relates to a connector unit.

2. Description of the Related Art

An example of a connector that provides electrical connection to an electronic device has an opening to be blocked when the connector is not connected to the electronic device.

Japanese Unexamined Patent Application Publication No. 2013-105048 (published May 30, 2013) discloses structures of an optical connector receptacle, an optical connection unit, and an optical outlet for providing an optical connector receptacle having a good dustproof performance and a simple structure.

A connector may have an opening to be blocked during installation and removable of an electronic device depending on the use of the electronic device. However, Japanese Unexamined Patent Application Publication No. 2013-105048 does not describe a technology for blocking the opening in the connector during installation and removable of the electronic device.

It is desirable to realize a connector unit including a connector and a connector cap that is easily attachable to and removable from the connector and that is not easily lost or left unattached to the connector.

SUMMARY

According to an aspect of the disclosure, there is provided a connector unit including a connector and a plurality of connector cap parts that are rotatably attached to a side wall of the connector. The connector cap parts each have a first space for receiving an end portion of the connector. The connector cap parts rotate toward the connector and are joined together to form a connector cap so that the first spaces communicate with each other to form a second space and that the end portion is placed in the second space.

DESCRIPTION OF THE EMBODIMENTS

First Embodiment

An embodiment of the present disclosure will now be described in detail.

Connector Unit 100

Figure 2:
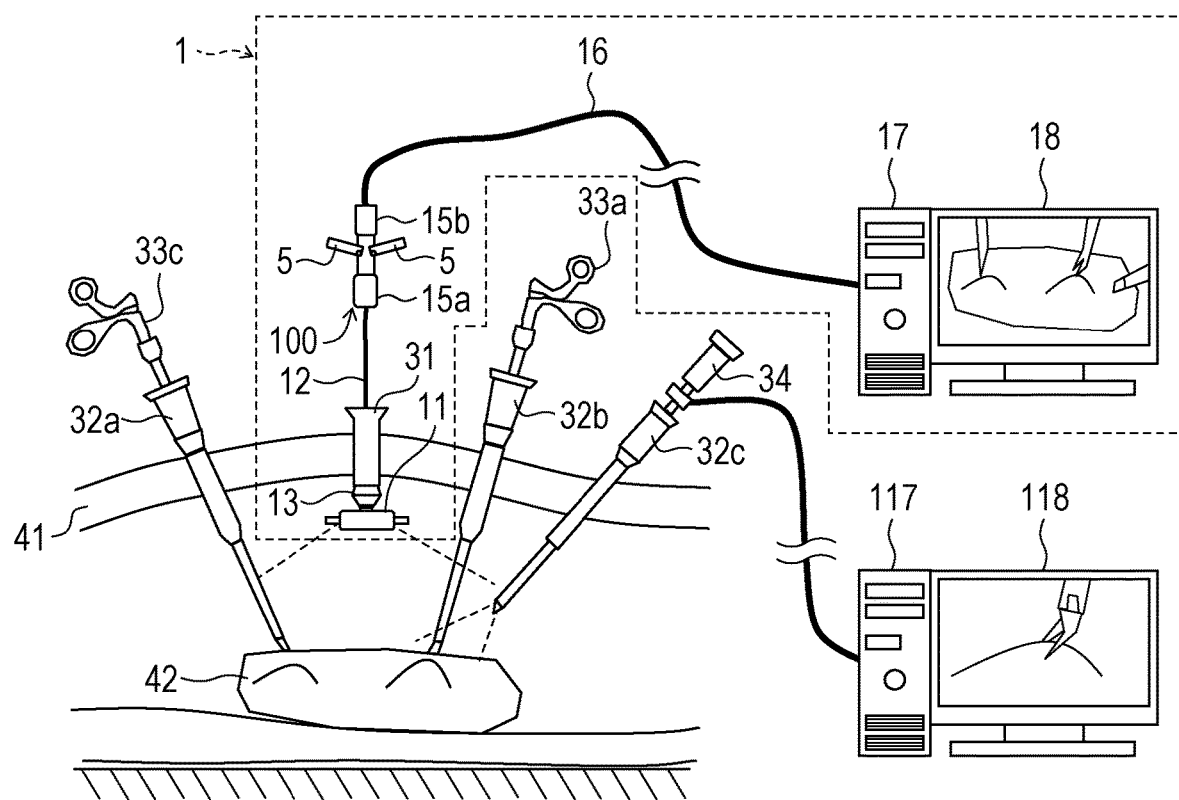
FIG. 2 is a schematic diagram illustrating an exemplary structure of an in-body monitoring camera system 1 according to the first embodiment of the present disclosure.

FIG. 2 is a schematic diagram illustrating an exemplary structure of an in-body monitoring camera system 1 according to the present embodiment. In the present embodiment, a connector unit 100 is applied to the in-body monitoring camera system 1. As illustrated in FIG. 2, a camera unit 11 is installed in a region inside an abdominal wall 41, that is, in the body. A camera cable connector 15a is inserted into the body and is then pulled out of the body to install the camera unit 11 in the body. The camera cable connector 15a is also inserted into the body and is then pulled out of the body to remove the camera unit 11 from the body. If a terminal of the camera cable connector 15a is wetted in the body during installation or removal of the camera unit 11, a contact failure of the camera cable connector 15a may occur. To avoid this, a connector cap 50 is attached to the camera cable connector 15a when the camera cable connector 15a is inserted into the body.

Figure 1A:
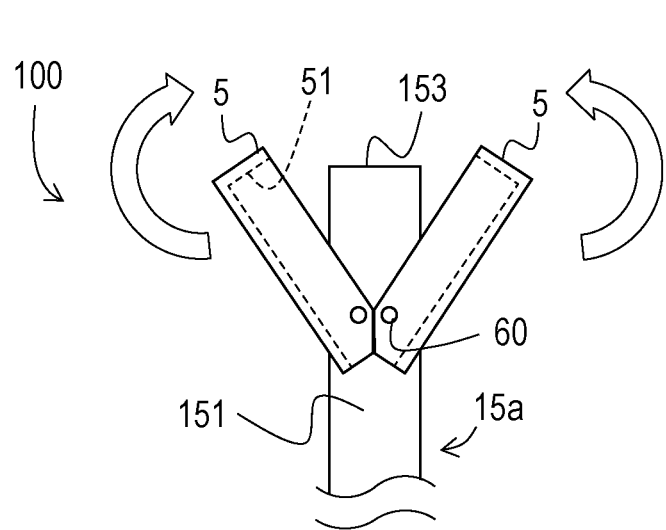
FIGS. 1A to 1D illustrate an exemplary structure of a connector unit according to a first embodiment of the present disclosure.
Figure 1B:
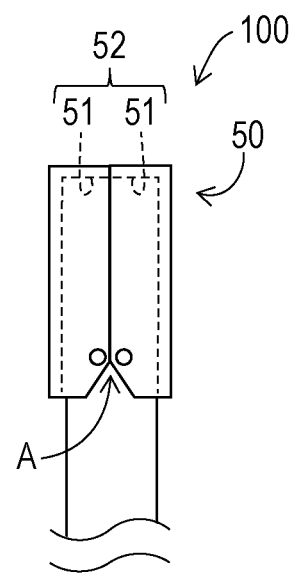
Figure 1C:
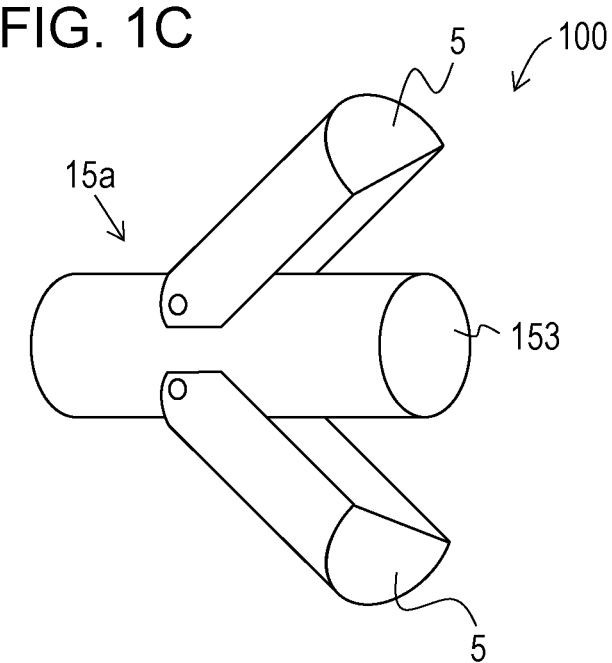
Figure 1D:
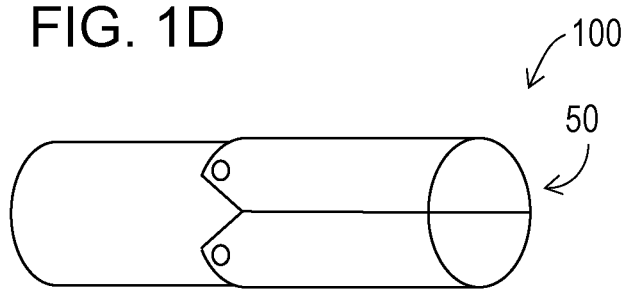

FIGS. 1A to 1D illustrate an exemplary structure of the connector unit 100 according to the present embodiment. More specifically, FIG. 1A is a front view of the connector unit 100 when the connector cap 50 is not attached to an end portion 153 of the camera cable connector 15a. FIG. 1B is a front view of the connector unit 100 when the connector cap 50 is attached to the end portion 153 of the camera cable connector 15a. FIG. 1C is a perspective view of the connector unit 100 when the connector cap 50 is not attached to the end portion 153 of the camera cable connector 15a. FIG. 1D is a perspective view of the connector unit 100 when the connector cap 50 is attached to the end portion 153 of the camera cable connector 15a.

As illustrated in FIGS. 1A to 1D, the connector unit 100 includes the camera cable connector 15a and a plurality of connector cap parts 5 that are rotatably attached to a side wall 151 of the camera cable connector 15a.

Camera Cable Connector 15a

The camera cable connector 15a is engageable with a device cable connector 15b and connects a camera cable 12 to a device cable 16. The camera cable connector 15a includes therein a terminal that provides the connection. As illustrated in FIGS. 1A to 1D, two connector cap parts 5 are connected to the side wall 151 of the camera cable connector 15a with hinges 60.

Connector Cap 50

The connector cap 50 is attached to the camera cable connector 15a and protects, for example, the terminal of the camera cable connector 15a.

As illustrated in FIGS. 1A to 1D, the connector cap 50 is formed of the two connector cap parts 5. As shown by the broken lines in FIGS. 1A and 1B, each of the two connector cap parts 5 has a first space 51 for receiving the end portion 153 of the camera cable connector 15a. As illustrated in FIG. 1A, the two connector cap parts 5 rotate toward the camera cable connector 15a about the respective hinges 60. As a result, as illustrated in FIG. 1B, the two connector cap parts 5 are joined together so that the first spaces 51 in the two connector cap parts 5 communicate with each other to form a second space 52. In other words, as illustrated in FIGS. 1B and 1D, the two connector cap parts 5 form the connector cap 50. The end portion 153 of the camera cable connector 15a is placed in the second space 52.

When the two connector cap parts 5 are rotated away from the camera cable connector 15a about the respective hinges 60 from the state in which the connector cap 50 is attached to the camera cable connector 15a, the connector cap 50 is removed from the camera cable connector 15a. To enable the two connector cap parts 5 to rotate away from the camera cable connector 15a about the respective hinges 60, the connector unit 100 has the following structure. That is, as illustrated in FIG. 1B, the two connector cap parts 5 are formed such that a gap A is provided therebetween in a region closer to a proximal end of the camera cable connector 15a than the hinges 60 are when the connector cap 50 is formed.

According to the above-described structure, the connector cap 50 can be formed simply by rotating the connector cap parts 5 toward the camera cable connector 15a. When the camera cable connector 15a is to be connected, the end portion 153 of the camera cable connector 15a can be separated from the connector cap 50 simply by rotating the connector cap parts 5 away from the camera cable connector 15a.

Thus, the connector cap 50 may be integrated with the camera cable connector 15a so that the connector cap 50 is not easily lost or left unattached to the camera cable connector 15a. In addition, the connector unit 100 including the connector cap 50 that can be easily attached to and separated from the camera cable connector 15a can be realized.

According to the above-described structure, the connector cap 50 can be formed by rotating the connector cap parts 5 toward the camera cable connector 15a. When the connector cap 50 is formed, the end portion 153 of the camera cable connector 15a is surrounded by the connector cap 50. Therefore, the camera cable connector 15a can be blocked from the outside over a larger region at a distal end thereof than in the case where, for example, the connector cap 50 is configured to cover only an opening at the distal end of the camera cable connector 15a. Therefore, the risk of image blurring or the like due to, for example, a contact failure or short circuiting caused when body fluid, body tissue, or the like comes into contact with the terminal provided at the distal end of the camera cable connector 15a can be effectively reduced.

In-Body Monitoring Camera System 1

The in-body monitoring camera system 1 will now be described in detail with reference to FIG. 2. The in-body monitoring camera system 1 is a medical system. As illustrated in FIG. 2, the in-body monitoring camera system 1 includes the camera unit 11 (in-body imaging device) that is introduced into the body and that is provided with the camera cable 12, a camera support tube 13 used to connect the camera unit 11 to a trocar 31 (tubular device) inserted into the body, a control system including a camera unit control device 17 and a display 18 (display device), and a device cable 16 that connects the camera cable 12 to the camera unit control device 17.

The camera cable 12 has the camera cable connector 15a at an end opposite to the end connected to the camera unit 11, and the device cable 16 has the device cable connector 15b at an end opposite to the end connected to the camera unit control device 17.

In the in-body monitoring camera system 1, an end portion of the trocar 31 that is inserted into the body through the abdominal wall 41 is connected to the camera support tube 13. Also, the camera unit 11 introduced into the body is joined to the camera support tube 13, and the camera cable connector 15a extends to the outside of the body through the camera support tube 13 and the trocar 31.

Method for Installing and Removing Camera Unit 11 into and from Body.

Figure 3A:
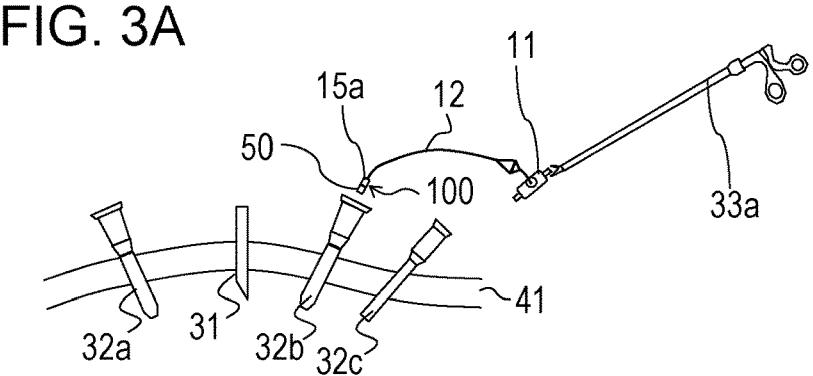
FIGS. 3A to 3F are schematic diagrams illustrating an example of a method for installing a camera unit according to the first embodiment of the present disclosure into the body.

A method for installing the camera unit 11 into the body will now be described in detail. FIGS. 3A to 3F are schematic diagrams illustrating an example of a method for installing the camera unit 11 into the body. As illustrated in FIG. 3A, first, an operator opens holes (ports) that enable a clamp or an endoscope to be inserted into a body cavity therethrough in the abdominal wall 41, and inserts trocars 32a to 32c through the ports. In addition, to install the camera unit 11 into the body cavity, the operator also opens a port in the abdominal wall 41 at a position where the entirety of an organ including an affected area can be observed, and inserts a trocar 31 through the port. More specifically, the trocar 31 is inserted through the abdominal wall 41 by inserting a needle-shaped obturator through the port while the obturator has the trocar 31 extending therethrough. The trocar 31 may have a small diameter to reduce invasiveness. More specifically, the trocar 31 may have a diameter of less than or equal to 3 mm. After inserting at least one of the trocars 32a to 32c and 31, the operator injects gas into the body through the at least one of the trocars to inflate the body cavity in advance and provide a space into which devices can be inserted.

Figure 3B:
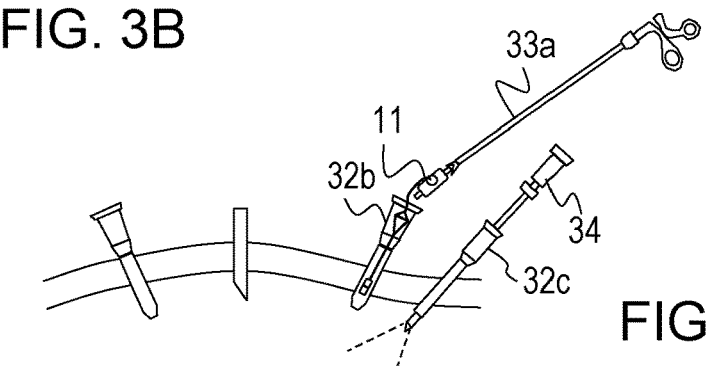

Next, as illustrated in FIG. 3B, the operator inserts an endoscope 34 into the body cavity through the trocar 32c, and performs the following steps while observing the body using the endoscope 34. First, the operator inserts the camera unit 11 held by a clamp 33a, the camera cable 12, the camera support tube 13, and the connector unit 100 into the body cavity through the trocar 32b. At this time, the connector cap 50 is attached to the camera cable connector 15a.

Figure 3C:
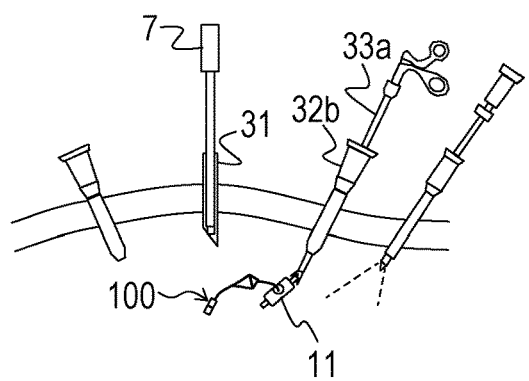

Next, as illustrated in FIG. 3C, the operator moves the camera unit 11 to a position near the trocar 31 by operating the clamp 33a and inserts an installation jig 7 into the body cavity through the trocar 31.

Figure 3D:
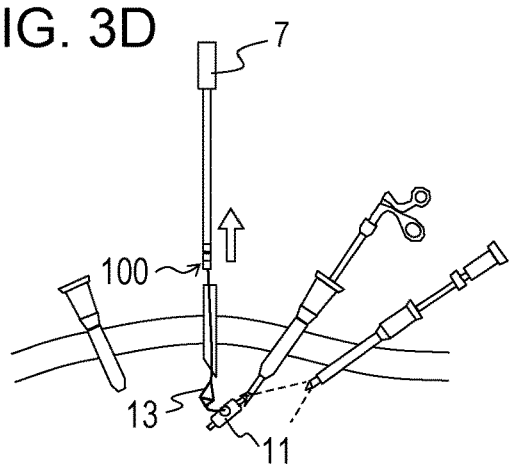

Next, as illustrated in FIG. 3D, the operator connects the installation jig 7 to the connector unit 100 and pulls the camera cable 12 out of the body. The camera cable 12 may instead be pulled out of the body by using, for example, a clamp.

Figure 3E:
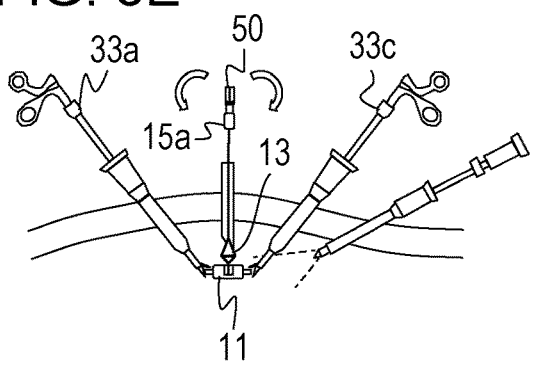
Figure 3F:
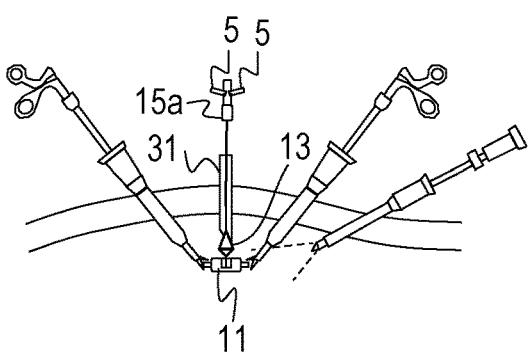

Next, as illustrated in FIGS. 3E and 3F, the connector cap parts 5 are rotated away from the camera cable connector 15a so that the connector cap 50 is removed from the end portion 153 of the camera cable connector 15a.

After the camera unit 11 is installed in the body, as illustrated in FIG. 2, the camera cable connector 15a is fitted to the device cable connector 15b so that the camera cable 12 is connected to the device cable 16. Accordingly, an image of a local region including the treated portion is displayed on a display 118 by an endoscope control device 117, and an image of the entirety of an organ 42 that is captured by the camera unit 11 is displayed on the display 18 by the camera unit control device 17.

Figure 4A:
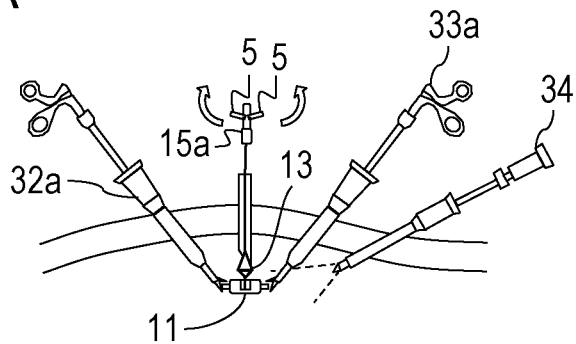
FIGS. 4A to 4D are schematic diagrams illustrating an example of a method for removing the camera unit according to the first embodiment of the present disclosure from the body.

A method for removing the camera unit 11 will now be described in detail. FIGS. 4A to 4D are schematic diagrams illustrating an example of a method for removing the camera unit 11 from the body. First, as illustrated in FIG. 4A, the connector cap parts 5, which are retained on the camera cable connector 15a at predetermined positions, are rotated toward the camera cable connector 15a. As a result, the connector cap 50 is attached to the end portion 153 of the camera cable connector 15a.

Figure 4B:
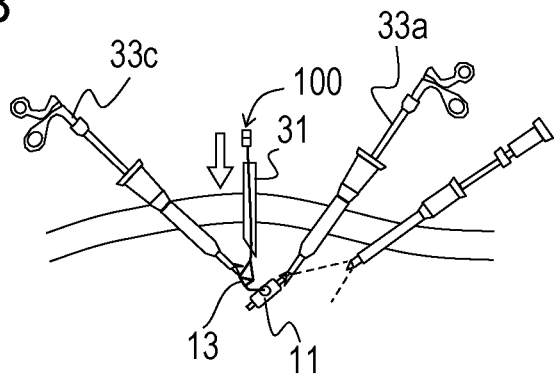
Figure 4C:
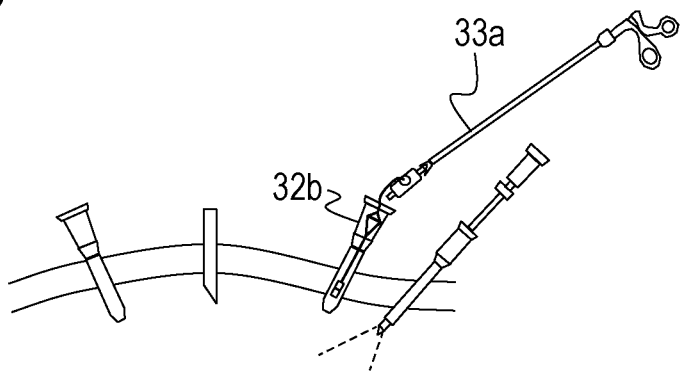
Figure 4D:
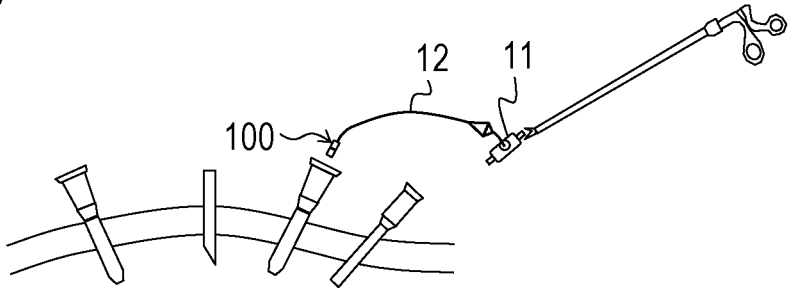

Next, as illustrated in FIG. 4B, the operator inserts a clamp 33c into a space between the camera support tube 13 and the camera unit 11 while holding the camera unit 11 in the body with the clamp 33a, and separates the camera support tube 13 from the camera unit 11 by using the clamp 33c. Next, as illustrated in FIGS. 4C and 4D, the operator pulls the camera support tube 13 away from the camera unit 11 and extracts the camera unit 11, the camera cable 12, the camera support tube 13, and the connector unit 100 out of the body through the trocar 32b. At this time, the camera cable 12 and the connector unit 100 are temporarily reinserted into the body through the trocar 31, and then pulled out of the body through the trocar 32b.

Second Embodiment

Another embodiment of the present disclosure will now be described. For convenience of description, members having the same functions as those of the members in the above-described embodiment are denoted by the same reference numerals, and description thereof is not repeated.

SUMMARY

In the present embodiment, each connector cap part 5 includes a first member 53 or a second member 54 for retaining the connector cap 50 in the attached state by using a magnetic force.

First Connector Cap Part 5a and Second Connector Cap Part 5b

Figure 5A:
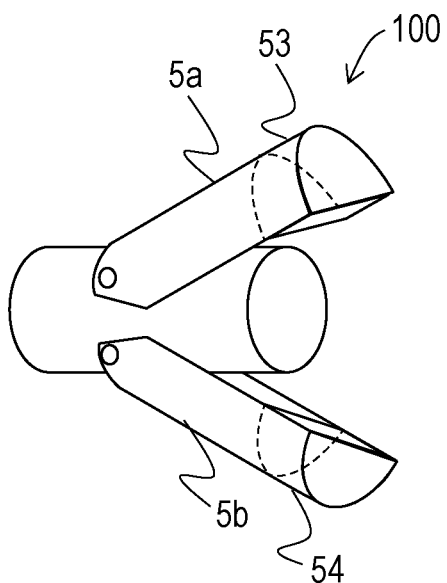
FIGS. 5A and 5B illustrate an exemplary structure of a connector unit according to a second embodiment of the present disclosure.
Figure 5B:
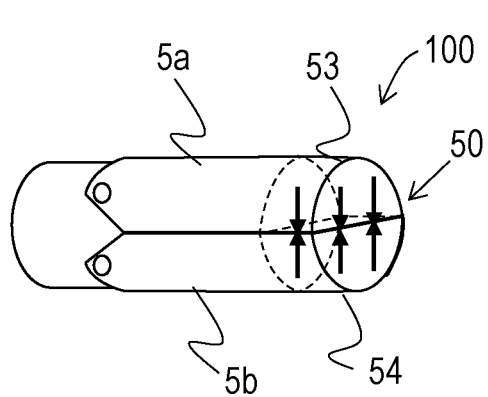

FIGS. 5A and 5B illustrate an exemplary structure of a connector unit 100 according to the present embodiment. As illustrated in FIGS. 5A and 5B, a connector cap 50 according to the present embodiment is formed of a first connector cap part 5a and a second connector cap part 5b.

The first member 53 is embedded in the first connector cap part 5a. The second member 54, which differs from the first member 53, is embedded in the second connector cap part 5b.

When the connector cap 50 is formed, that is, when the first connector cap part 5a and the second connector cap part 5b are joined together, the first member 53 and the second member 54 are arranged to face each other. In the example illustrated in FIGS. 5A to 5C, the first member 53 is provided at the distal end of the first connector cap part 5a.

Also, the second member 54 is provided at the distal end of the second connector cap part 5b.

The first member 53 is a magnetic material, and the second member 54 is a magnet. Therefore, as illustrated in FIG. 5B, when the connector cap 50 is formed, the first member 53 and the second member 54 are magnetically attracted to each other.

The structures of the first member 53 and the second member 54 of the connector cap 50 are not limited as long as the first member 53 and the second member 54 are attracted to each other. For example, the first member 53 and the second member 54 may both be magnets.

According to the above-described structure, the state in which the first connector cap part 5a and the second connector cap part 5b are joined together can be more reliably maintained by the magnetic force generated between the first member 53 and the second member 54. In other words, the state in which the connector cap 50 is formed (connector cap is attached) can be more reliably maintained. Therefore, the risk of separation of the connector cap 50 from the camera cable connector 15a that is not intended by the user can be more effectively reduced than in the case where the first member 53 and the second member 54 are not embedded. In addition, the connector cap 50 can be more stably attached to the camera cable connector 15a.

Figure 5C:
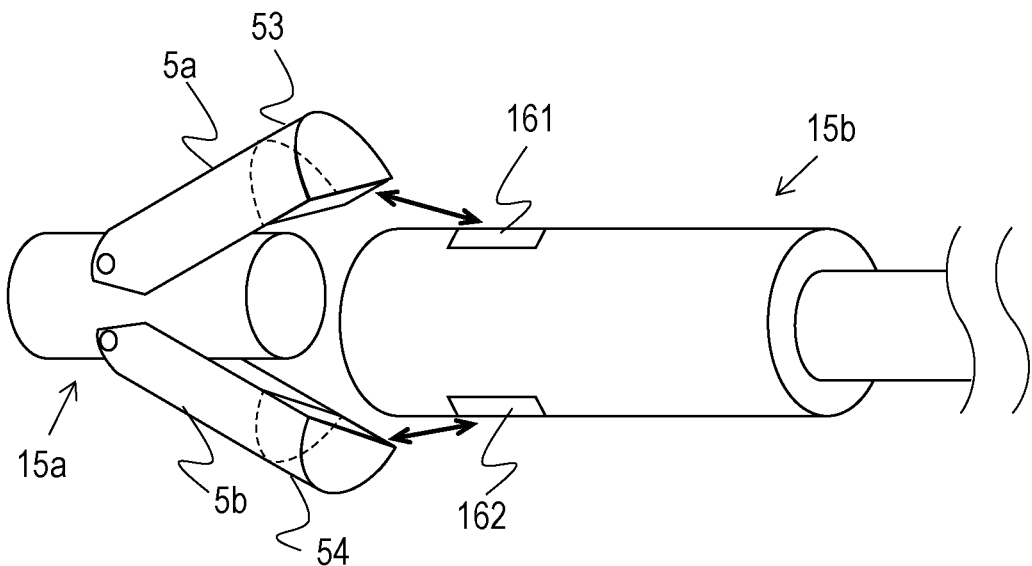
FIG. 5C illustrates an example of a connection between a camera cable connector and a device cable connector according to the second embodiment of the present disclosure.

Example of Connection Between Camera Cable Connector 15a and Device Cable Connector 15b FIG. 5C illustrates an example of a connection between the camera cable connector 15a and the device cable connector 15b according to the present embodiment.

The first connector cap part 5a and the second connector cap part 5b may be configured to clamp the device cable connector 15b when the camera cable connector 15a and the device cable connector 15b are connected to each other. In this case, the device cable connector 15b may, for example, be structured as follows. That is, as illustrated in FIG. 5C, a magnet 161 may be provided on the device cable connector 15b at a position where the first member 53 (magnetic material) comes into contact with the device cable connector 15b when the camera cable connector 15a and the device cable connector 15b are connected together. Also, a magnetic material 162 may be provided on the device cable connector 15b at a position where the second member 54 (magnet) comes into contact with the device cable connector 15b when the camera cable connector 15a and the device cable connector 15b are connected together.

According to the above-described structure, the connection strength between the camera cable connector 15a and the device cable connector 15b can be increased. Therefore, the risk of separation of the camera cable connector 15a and the device cable connector 15b that is not intended by the user can be reduced.

Third Embodiment

Another embodiment of the present disclosure will now be described. For convenience of description, members having the same functions as those of the members in the above-described embodiments are denoted by the same reference numerals, and description thereof is not repeated.

SUMMARY

In the present embodiment, each connector cap part 5 has a projection 56 or a recess 55. The projection 56 and the recess 55 engage with each other to retain the connector cap 50 in the attached state.

First Connector Cap Part 5a and Second Connector Cap Part 5b

Figure 6A:
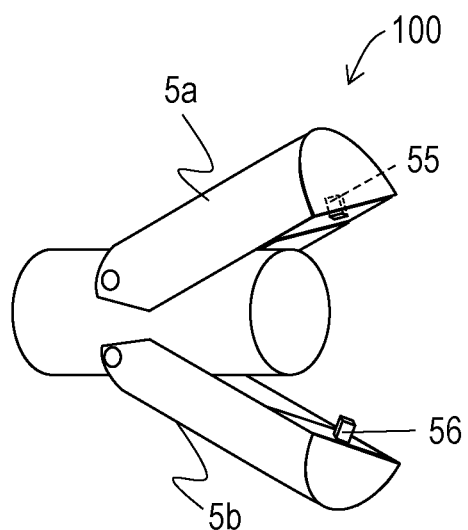
FIGS. 6A and 6B illustrate an exemplary structure of a connector unit according to a third embodiment of the present disclosure.
Figure 6B:
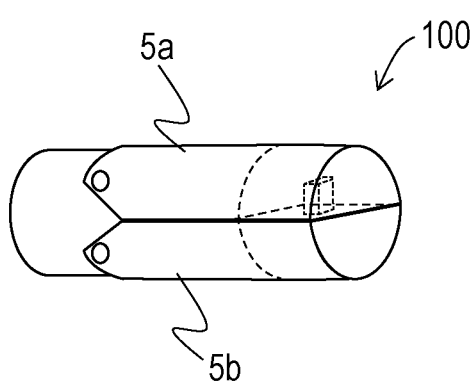

FIGS. 6A and 6B illustrate an exemplary structure of a connector unit 100 according to the present embodiment. As illustrated in FIGS. 6A and 6B, a connector cap 50 according to the present embodiment is formed of a first connector cap part 5a and a second connector cap part 5b.

At least one of the first connector cap part 5a and the second connector cap part 5b has the projection 56. At least the other one of the first connector cap part 5a and the second connector cap part 5b has the recess 55 that corresponds to the projection 56.

In the example illustrated in FIGS. 6A and 6B, the recess 55 is provided near the distal end of the first connector cap part 5a. Also, the projection 56 is provided near the distal end of the second connector cap part 5b. When the connector cap 50 is formed, that is, when the first connector cap part 5a and the second connector cap part 5b are joined together, the projection 56 and the recess 55 are arranged to face each other. Therefore, when the first connector cap part 5a and the second connector cap part 5b are joined together, the projection 56 and the recess 55 are fitted to each other.

According to the above-described structure, the state in which the connector cap 50 is attached can be more reliably maintained by fitting the projection and the recess to each other. Therefore, the risk of separation of the connector cap 50 from the camera cable connector 15a that is not intended by the user can be more effectively reduced than in the case where the projection 56 and the recess 55 are not formed. In addition, the connector cap 50 can be more stably attached to the camera cable connector 15a.

Figure 6C:
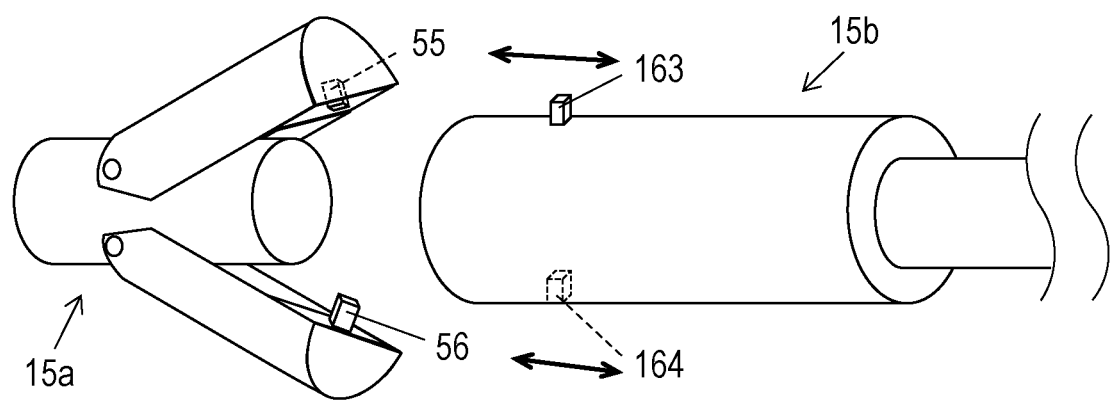
FIG. 6C illustrates an example of a connection between a camera cable connector and a device cable connector according to the third embodiment of the present disclosure.

Example of Connection Between Camera Cable Connector 15a and Device Cable Connector 15b FIG. 6C illustrates an example of a connection between the camera cable connector 15a and the device cable connector 15b according to the present embodiment.

The first connector cap part 5a and the second connector cap part 5b may be configured to clamp the device cable connector 15b when the camera cable connector 15a and the device cable connector 15b are connected to each other. In this case, the device cable connector 15b may, for example, be structured as follows. That is, as illustrated in FIG. 6C, a projection 163 may be provided on the device cable connector 15b at a position where the recess 55 comes into contact with the device cable connector 15b when the camera cable connector 15a and the device cable connector 15b are connected together. Also, a recess 164 may be provided on the device cable connector 15b at a position where the projection 56 comes into contact with the device cable connector 15b when the camera cable connector 15a and the device cable connector 15b are connected together. When the camera cable connector 15a and the device cable connector 15b are connected to each other, the recess 55 and the projection 163 become engageable with each other and the projection 56 and the recess 164 become engageable with each other.

According to the above-described structure, the connection strength between the camera cable connector 15a and the device cable connector 15b can be increased by fitting the recess 55 and the projection 163 to each other and fitting the projection 56 and the recess 164 to each other. Therefore, the risk of separation of the camera cable connector 15a and the device cable connector 15b that is not intended by the user can be reduced.

In addition, the user may consciously connect the camera cable connector 15a and the device cable connector 15b in positions such that the recess 55 in the first connector cap part 5a faces the projection 163 on the device cable connector 15b. Thus, the above-described structure provides a guide to cause the user to connect the camera cable connector 15a and the device cable connector 15b together in suitable positions. Therefore, the occurrence of troubles such as breakage due to connection between the camera cable connector 15a and the device cable connector 15b in incorrect positions can be reduced.

Fourth Embodiment

Another embodiment of the present disclosure will now be described. For convenience of description, members having the same functions as those of the members in the above-described embodiments are denoted by the same reference numerals, and description thereof is not repeated.

SUMMARY

A connector unit 100 according to the present embodiment includes a rotation urging unit 500 that rotates connector cap parts 5.

Rotation Urging Unit 500

The rotation urging unit 500 rotates the connector cap parts 5 in the same direction. For example, the rotation urging unit 500 rotates the connector cap parts 5 toward a camera cable connector 15a. As a result, an end portion 153 of the camera cable connector 15a is placed in a second space 52 in a connector cap 50.

According to the above-described structure, the connector cap parts 5 can be moved both toward and away from the camera cable connector 15a by the rotation urging unit 500. Therefore, the user can more easily attach and separate the connector cap 50 to and from the camera cable connector 15a than in the case where the rotation urging unit 500 is not provided.

Examples of the rotation urging unit 500 will now be described. FIGS. 7A to 7F illustrate exemplary structures of the rotation urging unit 500 according to the present embodiment.

First Example of Rotation Urging Unit 500

Figure 7A:
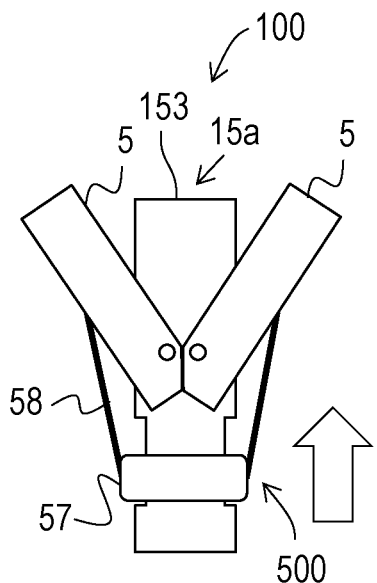
FIGS. 7A to 7F illustrate exemplary structures of a rotation urging unit according to a fourth embodiment of the present disclosure.
Figure 7B:
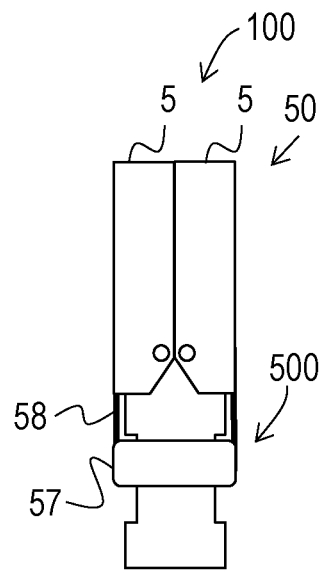

In an example illustrated in FIGS. 7A and 7B, the rotation urging unit 500 includes a slide portion 57 and operating portions 58. FIG. 7A illustrates the connector unit 100 when the connector cap 50 is not attached to the camera cable connector 15a. FIG. 7B illustrates the connector unit 100 when the connector cap 50 is attached to the camera cable connector 15a.

As illustrated in FIGS. 7A and 7B, the slide portion 57 is located closer to the proximal end of the camera cable connector 15a than the connector cap parts 5 are. The slide portion 57 slides in a direction along the center axis of the camera cable connector 15a. The slide portion 57 is connected to an end of each operating portion 58. The operating portions 58 may be, for example, wires. The slide portion 57 slides to apply a force to each operating portion 58 in the direction along the center axis of the camera cable connector 15a. Each operating portion 58 is connected to a corresponding one of the connector cap parts 5 at an end opposite to the end connected to the slide portion 57. When, for example, the user slides the slide portion 57 toward the proximal end of the camera cable connector 15a, the connector cap parts 5 are rotated away from the camera cable connector 15a. In other words, the connector cap 50 may be removed from the camera cable connector 15*a* by sliding the slide portion 57 toward the proximal end of the camera cable connector 15*a*.

In addition, when the user slides the slide portion 57 toward the distal end of the camera cable connector 15*a*, the connector cap parts 5 are rotated toward the camera cable connector 15*a*. In other words, the connector cap 50 may be attached to the camera cable connector 15*a* by sliding the slide portion 57 toward the distal end of the camera cable connector 15*a*. The direction toward the distal end of the camera cable connector 15*a* is the direction indicated by the arrow in FIG. 7A.

Second Example of Rotation Urging Unit 500

Figure 7C:
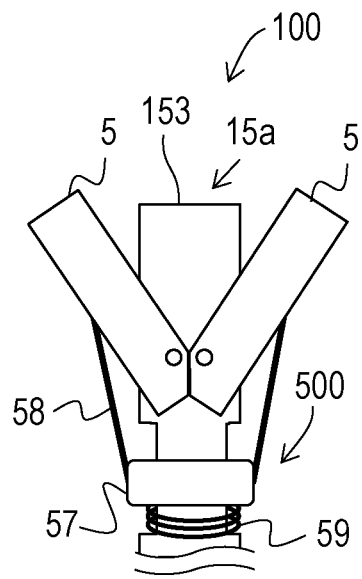
Figure 7D:
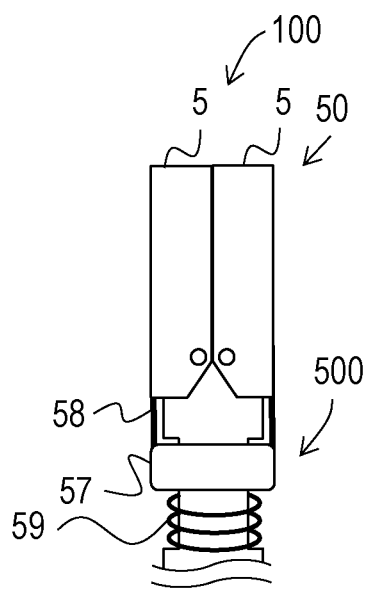

An example of the rotation urging unit 500 illustrated in FIGS. 7C and 7D includes an elastic body 59 in addition to the above-described structure of the rotation urging unit 500 according to the first example of the rotation urging unit 500. In this example, the elastic body 59 is a spring.

FIG. 7C illustrates the connector unit 100 when the connector cap 50 is not attached to the camera cable connector 15*a*. FIG. 7D illustrates the connector unit 100 when the connector cap 50 is attached to the camera cable connector 15*a*.

The elastic body 59 is located adjacent to the slide portion 57 and closer to the proximal end of the camera cable connector 15*a* than the slide portion 57 is. When the slide portion 57 slides toward the proximal end of the camera cable connector 15*a*, the elastic body 59 exerts a force that pushes the slide portion 57 toward the distal end of the camera cable connector 15*a*.

When, for example, the user slides the slide portion 57 toward the proximal end of the camera cable connector 15*a*, the connector cap parts 5 are rotated away from the camera cable connector 15*a*. In other words, the connector cap 50 is removed from the camera cable connector 15*a*.

Then, when the user removes their hand from the slide portion 57, the elastic body 59 causes the slide portion 57 to slide toward the distal end of the camera cable connector 15*a*. Accordingly, the connector cap parts 5 are rotated toward the camera cable connector 15*a*. In other words, the connector cap 50 is attached to the camera cable connector 15*a*.

When the camera cable connector 15*a* and the device cable connector 15*b* are disconnected from each other, the connector cap 50 is automatically attached to the camera cable connector 15*a* by the elastic body 59.

Third Example of Rotation Urging Unit 500

Figure 7E:
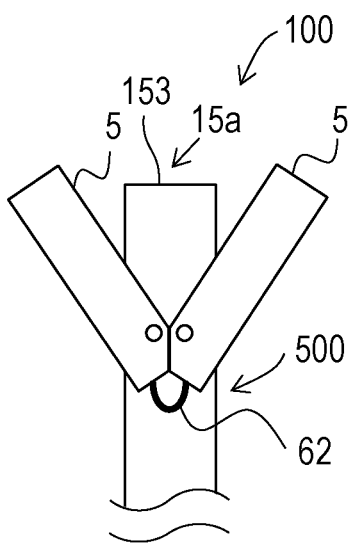
Figure 7F:
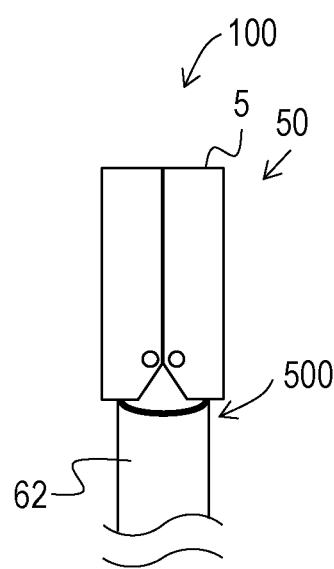

An example of the rotation urging unit 500 of the connector unit 100 illustrated in FIGS. 7E and 7F includes an elastic body 62. FIG. 7E illustrates the connector unit 100 when the connector cap 50 is not attached to the camera cable connector 15*a*. FIG. 7F illustrates the connector unit 100 when the connector cap 50 is attached to the camera cable connector 15*a*.

The elastic body 62 is located between the connector cap parts 5 and closer to the proximal end of the camera cable connector 15*a* than the hinges 60 are. The elastic body 62 is, for example, a spring. The elastic body 62 applies a force to the connector cap parts 5 so that the ends of the connector cap parts 5 that are closer to the proximal end of the camera cable connector 15*a* than the hinges 60 are move away from each other. Accordingly, when no force is applied to the connector cap parts 5, the connector cap 50 is attached to the camera cable connector 15*a*. When a force is applied to the connector cap parts 5 so that the ends of the connector cap parts 5 at which the elastic body 62 is provided move toward each other, the connector cap 50 is removed from the camera cable connector 15*a*.

When the camera cable connector 15*a* and the device cable connector 15*b* are disconnected from each other, the connector cap 50 is automatically attached to the camera cable connector 15*a* by the elastic body 62.

The above-described second example of the rotation urging unit 500 and the third example of the rotation urging unit 500 may be described as having the following structure.

That is, the connector cap parts 5 are provided with the elastic body 59 or the elastic body 62 that serves as the rotation urging unit. The elastic body 59 or the elastic body 62 exerts an urging force that urges the connector cap parts 5 toward the camera cable connector 15*a*.

Modification

An example of an operation in which the connector cap 50 is attached to the camera cable connector 15*a* by the trocar 31 will be described with reference to FIGS. 8A to 8C. In this example, the trocar 31 serves as the rotation urging unit.

Figure 8A:
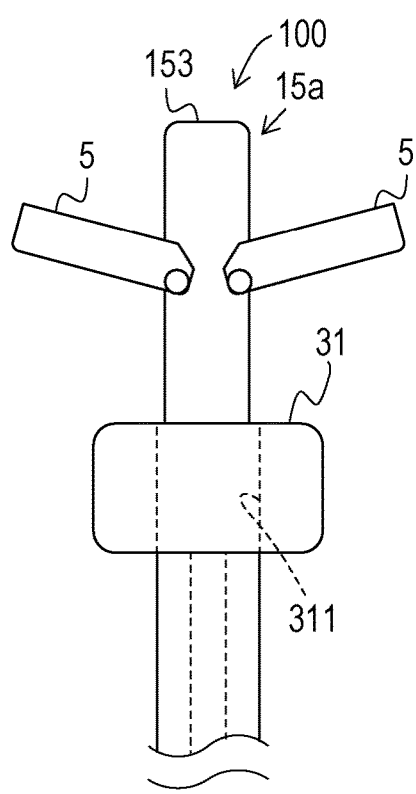
FIGS. 8A to 8C illustrate an example of an operation of a connector unit according to a modification of the fourth embodiment of the present disclosure.
Figure 8B:
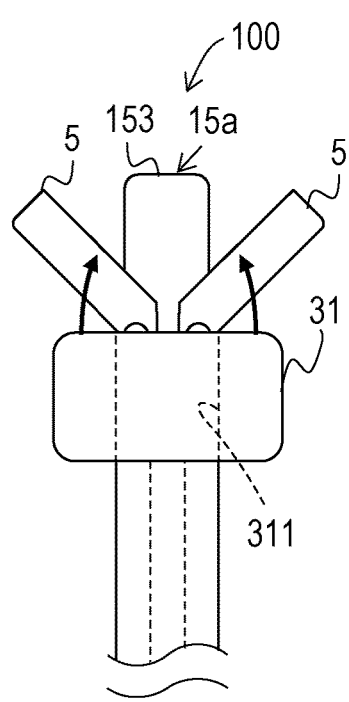
Figure 8C:
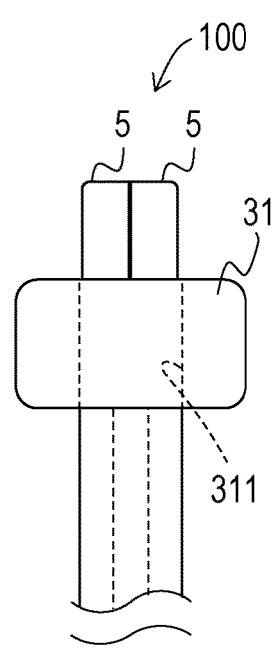

FIGS. 8A to 8C illustrate an example of an operation of a connector unit 100. The connector unit 100 of this example may have the structure of the connector unit 100 according to the first embodiment.

As illustrated in FIGS. 8A to 8C, the trocar 31 has a hollow space 311. The camera cable connector 15*a* extends through the hollow space 311 so that the trocar 31 is slidable with respect to the camera cable connector 15*a* in the direction of the center axis of the camera cable connector 15*a*. In other words, when the camera cable connector 15*a* is inserted into the trocar 31, the trocar 31 is slid in the direction of the center axis of the camera cable connector 15*a*.

After the trocar 31 starts to slide toward the connector cap parts 5 and before at least portions of the connector cap parts 5 are placed in the hollow space 311, the following operation is carried out. That is, the connector cap parts 5 rotate toward the camera cable connector 15*a*, and the end portion 153 is placed in the second space 52. In other words, the connector cap 50 is attached to the camera cable connector 15*a*.

According to the above-described structure, the end portion 153 of the camera cable connector 15*a* can be placed in the second space 52 simply by sliding the trocar 31 toward the connector cap parts 5 and placing at least portions of the connector cap parts 5 in the hollow space 311.

In addition, the end portion 153 of the camera cable connector 15*a* can be separated from the connector cap 50 simply by sliding the trocar 31 away from the connector cap parts 5.

Fifth Embodiment

Another embodiment of the present disclosure will now be described. For convenience of description, members having the same functions as those of the members in the above-described embodiments are denoted by the same reference numerals, and description thereof is not repeated.

SUMMARY

According to the present embodiment, connector cap parts 5 are each provided with an elastic body 61 that serves as a rotation urging unit. The connector cap parts 5 each receive an urging force from the elastic body 61, and thereby clamp the device cable connector 15*b* provided at an end of a cable to be connected.

Connector Unit 100

Figure 9A:
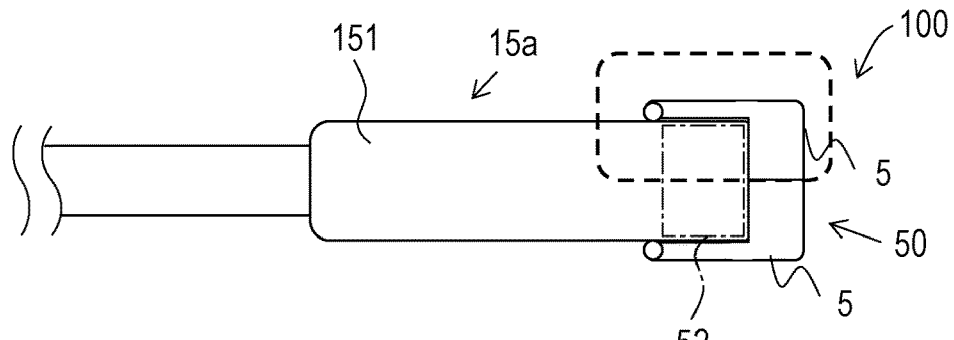
FIGS. 9A to 9D illustrate an exemplary structure of a connector unit according to a fifth embodiment of the present disclosure.
Figure 9B:
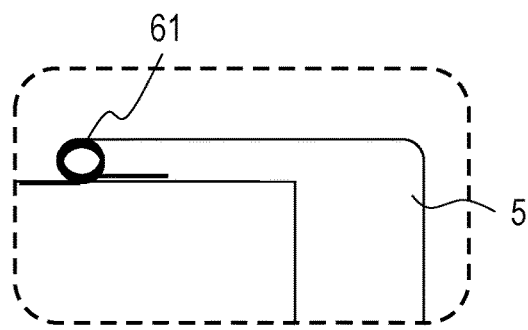
Figure 9C:
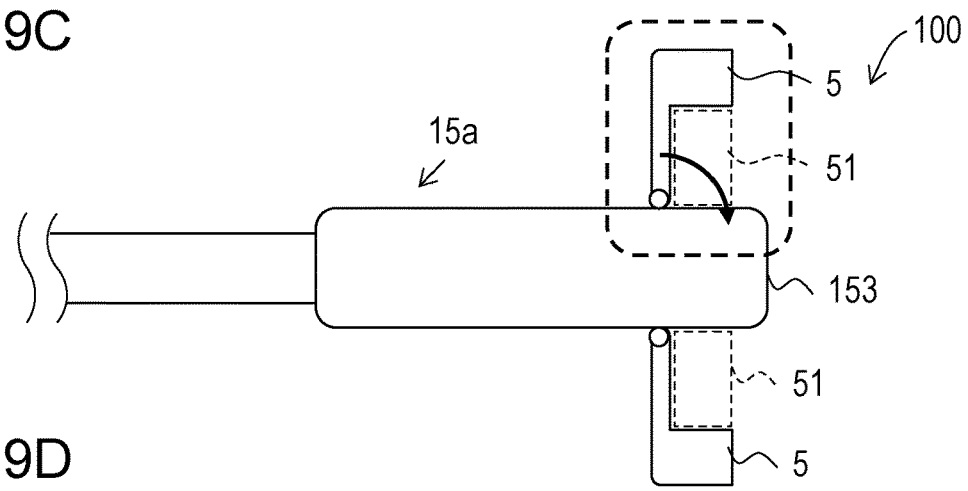
Figure 9D:
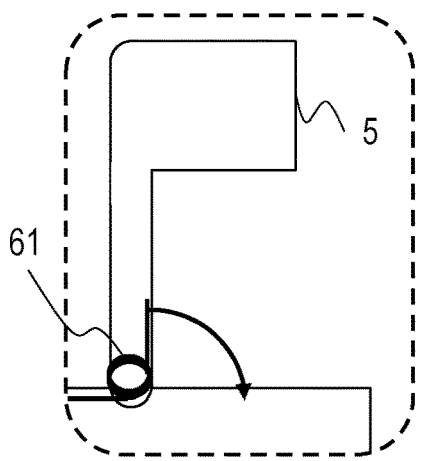

FIGS. 9A to 9D illustrate an exemplary structure of a connector unit 100 according to the present embodiment. More specifically, FIG. 9A illustrates a state in which a connector cap 50 is attached to a camera cable connector 15a. FIG. 9B is an enlarged view of the region surrounded by the broken line in FIG. 9A. FIG. 9C illustrates a state in which the connector cap 50 is removed from the camera cable connector 15a. FIG. 9D is an enlarged view of the region surrounded by the broken line in FIG. 9C.

As illustrated in FIGS. 9A and 9C, the connector unit 100 includes the camera cable connector 15a and a plurality of connector cap parts 5 that are rotatably attached to a side wall 151 of the camera cable connector 15a.

As shown by the broken lines in FIG. 9C, each of the two connector cap parts 5 has a first space 51 that receives an end portion 153 of the camera cable connector 15a. The two connector cap parts 5 rotate toward the camera cable connector 15a. As a result, as illustrated in FIG. 9A, the two connector cap parts 5 are joined together so that the first spaces 51 of the two connector cap parts 5 communicate with each other and form a second space 52. In other words, as illustrated in FIG. 9A, the two connector cap parts 5 form the connector cap 50. The end portion 153 of the camera cable connector 15a is placed in the second space 52.

Elastic Body 61

As illustrated in FIGS. 9B and 9D, each connector cap part 5 is provided with the elastic body 61 that serves as a rotation urging unit. The elastic body 61 exerts an urging force that urges the corresponding connector cap part 5 toward the camera cable connector 15a. The arrows shown in FIGS. 9C and 9D indicate the direction in which the connector cap part 5 is rotated by the urging force. The elastic body 61 may be, for example, a torsion spring.

According to the above-described structure, each connector cap part 5 can be automatically rotated toward the camera cable connector 15a by the urging force of the elastic body 61. Therefore, the connector cap 50 can be more easily attached to the camera cable connector 15a than in the case where the elastic body 61 is not provided as a rotation urging unit.

Figure 10A:
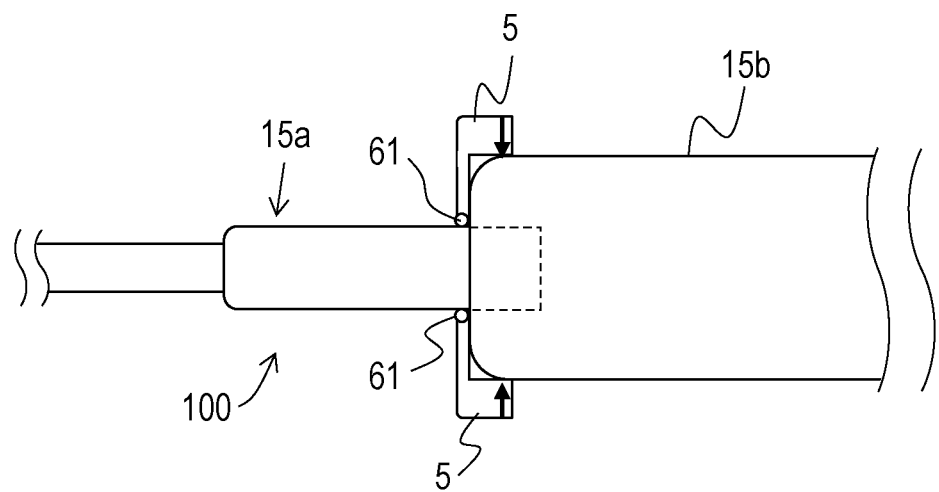
FIGS. 10A and 10B illustrate an example of a connection between a camera cable connector and a device cable connector according to the fifth embodiment of the present disclosure.
Figure 10B:
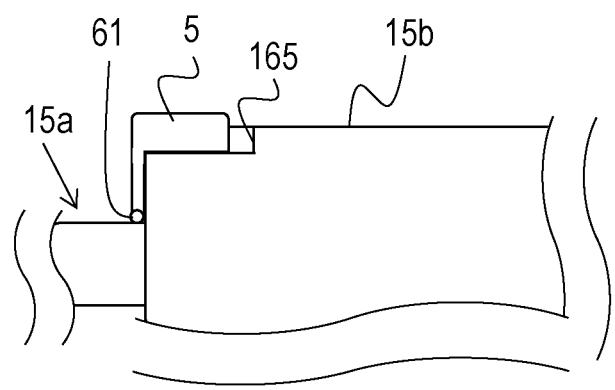

Example of Connection Between Camera Cable Connector 15a and Device Cable Connector 15b FIGS. 10A and 10B illustrate an example of a connection between the camera cable connector 15a and the device cable connector 15b according to the present embodiment.

As illustrated in FIG. 10A, when the camera cable connector 15a and the device cable connector 15b are connected to each other, the connector cap parts 5 of the connector unit 100 may clamp an end of the device cable connector 15b.

According to the above-described structure, the end of the device cable connector 15b is clamped by the connector cap parts 5 while the camera cable connector 15a and the device cable connector 15b are connected together. Therefore, the camera cable connector 15a and the device cable connector 15b can be strongly connected together.

The device cable connector 15b may have the following structure. That is, as illustrated in FIG. 10B, the device cable connector 15b may have a groove 165 to which one of the connector cap parts 5 is fitted when the camera cable connector 15a and the device cable connector 15b are connected together.

According to the above-described structure, the user may consciously connect the camera cable connector 15a and the device cable connector 15b in positions such that the first connector cap part 5a faces the groove 165 in the device cable connector 15b. Thus, the above-described structure provides a guide to cause the user to connect the camera cable connector 15a and the device cable connector 15b together in suitable positions. The structure may be such that the camera cable connector 15a and the device cable connector 15b are not easily connected together when the first connector cap part 5a is not fitted to the groove 165.

Sixth Embodiment

Another embodiment of the present disclosure will now be described. For convenience of description, members having the same functions as those of the members in the above-described embodiments are denoted by the same reference numerals, and description thereof is not repeated.

Connector Cap 50 and Installation Jig 7

According to the method for installing the camera unit 11 into the body of the first embodiment, the camera cable 12 is pulled out of the body by connecting the installation jig 7 to the connector unit 100.

In the present embodiment, exemplary structures of the installation jig 7 used to pull out the connector unit 100 that has been inserted into the body and exemplary structures of the connector cap 50 that is connectable to the installation jig 7 will be described with reference to FIGS. 11A to 11D.

FIGS. 11A to 11D illustrate examples of the connector cap 50 and the installation jig 7.

Figure 11A:
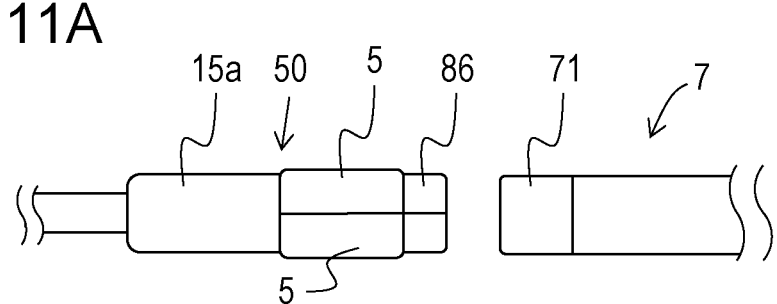
FIGS. 11A to 11D illustrate examples of connector caps and installation jigs according to a sixth embodiment of the present disclosure.

In the example illustrated in FIG. 11A, the connector cap 50 includes a magnet portion 86 at an end thereof. In addition, the installation jig 7 also includes a magnet portion 71 at an end thereof. The magnet portion 71 of the installation jig 7 and the magnet portion 86 of the connector cap 50 are connected to each other by a magnetic force in the body.

Figure 11B:
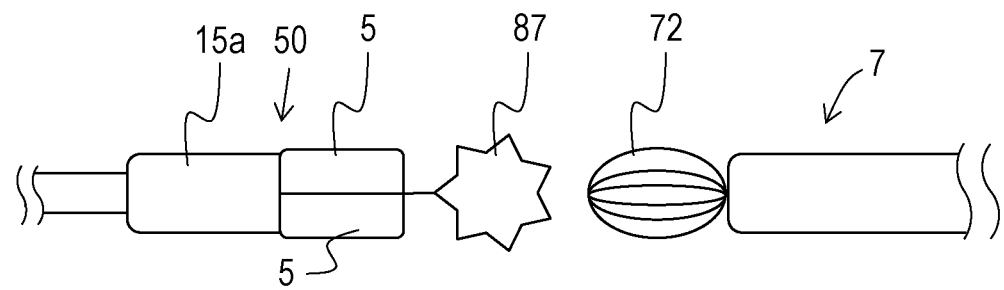

In the example illustrated in FIG. 11B, the connector cap 50 includes an engagement device 87 at an end thereof. In addition, the installation jig 7 includes a beater-shaped end portion 72 at an end thereof. The beater-shaped end portion 72 is formed of a plurality of curved retaining wires that are connected to each other at both ends thereof, and has an ellipsoidal (spheroidal) shape. The retaining wires can be deformed by applying an external force. The beater-shaped end portion 72 may be configured to be pulled into a tubular rod-shaped portion by an end-portion-driving hard wire when a handle lever (not shown) is operated. The beater-shaped end portion 72 expands in the shape of a beater so that the gaps between the retaining wires are increased when no force is applied thereto. When the lever is pulled to apply a force that pulls the beater-shaped end portion 72 into the tubular rod-shaped portion, the gaps between the retaining wires are reduced. Thus, the gaps between the retaining wires that form the beater-shaped end portion 72 are changeable.

More specifically, the size of the gaps between the retaining wires in the state in which the beater-shaped end portion 72 is outside the tubular rod-shaped portion may correspond to the diameter of the engagement device 87. In such a case, when the engagement device 87 is pressed against the beater-shaped end portion 72, the engagement device 87 may be inserted into the beater-shaped end portion 72 and restrained from moving out of the beater-shaped end portion 72.

Figure 11C:
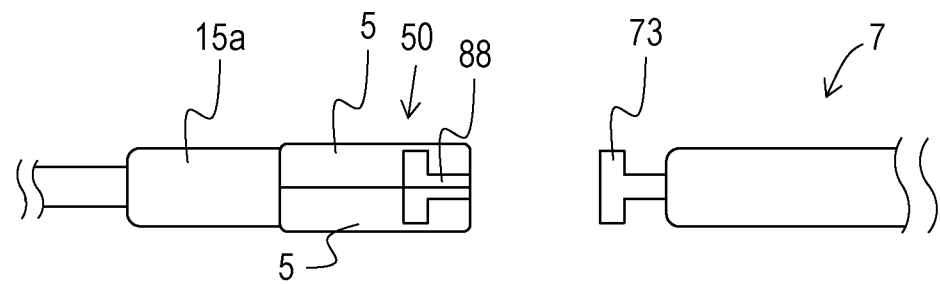

In the example illustrated in FIG. 11C, the connector cap 50 includes a second connecting portion 88 at an end thereof. In addition, the installation jig 7 includes a fitting portion 73 at an end thereof. The second connecting portion 88 of the connector cap 50 has a recessed shape that corresponds to the shape of the fitting portion 73 of the installation jig 7. The installation jig 7 and the connector cap 50 are connected to each other by fitting the fitting portion 73 to the second connecting portion 88 having the recessed shape.

Figure 11D:
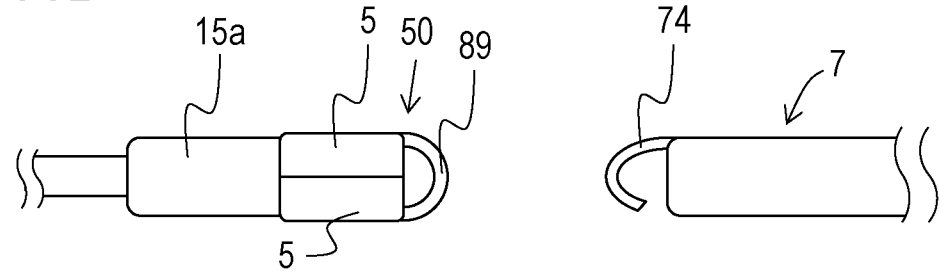

In the example illustrated in FIG. 11D, the connector cap 50 includes a hook-receiving portion 89 at an end thereof. In addition, the installation jig 7 includes a hook 74 at an end thereof. The installation jig 7 and the connector cap 50 are connected to each other by engaging the hook 74 of the installation jig 7 with the hook-receiving portion 89 of the connector cap 50.

The connecting force between the connector cap 50 and the camera cable connector 15a may be designed to be greater than the connecting force between the installation jig 7 and the connector cap 50.

SUMMARY

A connector unit (100) according to a first aspect of the present disclosure includes a connector (camera cable connector 15a) and a plurality of connector cap parts (5) that are rotatably attached to a side wall (151) of the connector. The connector cap parts each have a first space (51) for receiving an end portion of the connector (153). The connector cap parts rotate toward the connector and are joined together to form a connector cap (50) so that the first spaces communicate with each other to form a second space (52) and that the end portion is placed in the second space.

According to the above-described structure, the connector cap can be formed simply by rotating the connector cap parts toward the connector. When the connector is to be connected, the end portion of the connector can be separated from the connector cap simply by rotating the connector cap parts away from the connector.

Thus, a connector unit including a connector cap that is integrated with a connector so that the connector cap is not easily lost or left unattached to the connector and that can be easily attached to and separated from the connector can be realized.

In addition, according to the above-described structure, when the connector cap is formed by rotating the connector cap parts toward the connector, the end portion of the connector is surrounded by the connector cap. Therefore, the connector can be blocked from the outside over a larger region at a distal end thereof than in the case where, for example, the connector cap is configured to cover only an opening of the terminal at the distal end of the connector. Therefore, the risk of image blurring or the like due to, for example, a contact failure or short circuiting caused when body fluid, body tissue, or the like comes into contact with the terminal provided at the distal end of the connector can be effectively reduced.

In this specification, the term "separate" means to rotate the connector cap parts away from the connector so that the end portion of the connector that has been placed in the second space of the connector cap is exposed to the outside.

According to a second aspect of the present disclosure, in the connector unit according to the first aspect, the connector cap parts may include a first connector cap part (5a) and a second connector cap part (5b). A first member (53) is embedded in the first connector cap part. A second member (54) that differs from the first member is embedded in the second connector cap part at a position such that the second member faces the first member when the first connector cap part and the second connector cap part are joined together. The first member and the second member are attracted to each other by a magnetic force.

According to the above-described structure, the state in which the first connector cap part and the second connector cap part are joined together can be more reliably maintained by the magnetic force generated between the first member and the second member. In other words, the state in which the connector cap is formed (connector cap is attached) can be more reliably maintained. Therefore, the risk of separation of the connector cap from the connector that is not intended by the user can be more effectively reduced than in the case where the first member and the second member are not embedded. In addition, the connector cap can be more stably attached to the connector.

According to a third aspect of the present disclosure, in the connector unit according to the first or second aspect, the connector cap parts may include a first connector cap part and a second connector cap part. At least one of the first connector cap part and the second connector cap part includes a projection (56), and at least another one of the first connector cap part and the second connector cap part has a recess (55) that corresponds to the projection. The projection and the recess are fitted to each other when the first connector cap part and the second connector cap part are joined together.

According to the above-described structure, the state in which the connector cap is attached can be more reliably maintained by fitting the projection and the recess to each other. Therefore, the risk of separation of the connector cap from the connector that is not intended by the user can be more effectively reduced than in the case where the projection and the recess are not formed. In addition, the connector cap can be more stably attached to the connector.

According to a fourth aspect of the present disclosure, the connector unit according to any one of the first to third aspects may further include a rotation urging unit (500) that rotates the connector cap parts in the same direction. The end portion is placed in the second space when the rotation urging unit rotates the connector cap parts toward the connector.

According to the above-described structure, the connector cap parts can be moved both toward and away from the connector by the rotation urging unit. Therefore, the connector cap can be more easily attached to and separated from the connector than in the case where the rotation urging unit is not provided.

According to a fifth aspect of the present disclosure, in the connector unit according to the fourth aspect, the rotation urging unit (trocar 31) may have a hollow space (311). The connector extends through the hollow space so that the rotation urging unit is slidable in a direction of a center axis of the connector. The connector cap parts rotate toward the connector and the end portion is placed in the second space after the rotation urging unit starts to slide toward the connector cap parts and before at least portions of the connector cap parts are placed in the hollow space.

According to the above-described structure, the end portion of the connector can be placed in the second space simply by sliding the rotation urging unit toward the connector cap parts and placing at least portions of the connector cap parts in the hollow space. In addition, the end portion of the connector can be separated from the connector cap simply by sliding the rotation urging unit away from the connector cap parts.

According to a sixth aspect of the present disclosure, in the connector unit according to the fourth aspect, the connector cap parts may be provided with an elastic body (59, 61, 62) that serves as the rotation urging unit. The elastic body exerts an urging force that urges the connector cap parts toward the connector.

According to the above-described structure, each connector cap part can be automatically rotated toward the connector by the urging force of the elastic body. Therefore, the connector cap can be more easily attached to the connector than in the case where the elastic body is not provided as the rotation urging unit.

According to a seventh aspect of the present disclosure, in the connector unit according to the sixth aspect, when the connector is connected to a cable to be connected, the connector cap parts clamp an end of the cable connected to the connector.

According to the above-described structure, the connector and the cable can be strongly connected together by clamping the end of the cable with the connector cap parts while the connector and the cable are connected together.

A connector cap according to an eighth aspect of the present disclosure includes a plurality of connector cap parts that are rotatably attached to a side wall of a connector. The connector cap parts each have a first space for receiving an end portion of the connector. The connector cap parts rotate toward the connector and are joined together to form the connector cap so that the first spaces communicate with each other to form a second space and that the end portion is placed in the second space. This structure provides effects similar to those of the above-described first aspect.

The present disclosure is not limited to the above-described embodiments, and various modifications are possible within the scope of the claims. An embodiment obtained by appropriately combining technical means disclosed in different embodiments is also included in the technical scope of the present disclosure. Also, a new technical feature may be obtained by combining technical means disclosed in the embodiments.

The present disclosure contains subject matter related to that disclosed in Japanese Priority Patent Application JP 2018-069144 filed in the Japan Patent Office on Mar. 30, 2018, the entire contents of which are hereby incorporated by reference.

It should be understood by those skilled in the art that various modifications, combinations, sub-combinations and alterations may occur depending on design requirements and other factors insofar as they are within the scope of the appended claims or the equivalents thereof.

What is claimed is:

1. A connector unit comprising:
   a connector;
   a first connector cap part and a second connector cap part each of which is rotatably attached to a side wall of the connector, and
   a rotation urging unit that rotates the connector cap parts in a same direction,
   wherein the first connector cap part and the second connector cap part each have a first space for receiving an end portion of the connector,
   wherein the first connector cap part and the second connector cap part rotate toward the connector and are joined together to form a connector cap so that the first spaces communicate with each other to form a second space and that the end portion is placed in the second space,
   wherein at least one of the first connector cap part and the second connector cap part includes a projection, and at least another one of the first connector cap part and the second connector cap part has a recess that corresponds to the projection,
   wherein the projection and the recess are fitted to each other when the first connector cap part and the second connector cap part are joined together,
   wherein the end portion is placed in the second space when the rotation urging unit rotates the connector cap parts toward the connector,
   wherein the rotation urging unit has a hollow space,
   wherein the connector extends through the hollow space so that the rotation urging unit is slidable in a direction of a center axis of the connector, and
   wherein the connector cap parts rotate toward the connector and the end portion is placed in the second space after the rotation urging unit starts to slide toward the connector cap parts and before at least portions of the connector cap parts are placed in the hollow space.

2. A connector unit comprising:
   a connector; and
   a plurality of connector cap parts that are rotatably attached to a side wall of the connector,
   wherein the connector cap parts each have a first space for receiving an end portion of the connector, and a rotation urging unit that rotates the connector cap parts in a same direction,
   wherein the connector cap parts rotate toward the connector and are joined together to form a connector cap so that the first spaces communicate with each other to form a second space and that the end portion is placed in the second space,
   wherein the end portion is placed in the second space when the rotation urging unit rotates the connector cap parts toward the connector,
   wherein the connector cap parts are provided with an elastic body that serves as the rotation urging unit,
   wherein the elastic body exerts an urging force that urges the connector cap parts toward the connector,
   wherein, when the connector is connected to a cable to be connected, the connector cap parts clamp an end of the cable connected to the connector,
   wherein the end of the cable to be connected to the connector has a groove to which one of the connector cap parts is finable, and
   wherein the connector is connectable to the cable to be connected when the one of the connector cap parts is fitted to the groove.

3. A connector unit comprising:
   a connector; and
   a plurality of connector cap parts that are rotatably attached to a side wall of the connector,
   wherein the connector cap parts each have a first space for receiving an end portion of the connector,
   a rotation urging unit that rotates the connector cap parts in a same direction,
   wherein the connector cap parts rotate toward the connector and are joined together to form a connector cap so that the first spaces communicate with each other to form a second space and that the end portion is placed in the second space,
   wherein the end portion is placed in the second space when the rotation urging unit rotates the connector cap parts toward the connector,
   wherein the rotation urging unit has a hollow space,
   wherein the connector extends through the hollow space so that the rotation urging unit is slidable in a direction of a center axis of the connector, and wherein the connector cap parts rotate toward the connector and the end portion is placed in the second space after the rotation urging unit starts to slide toward the connector cap parts and before at least portions of the connector cap parts are placed in the hollow space.

4. The connector unit according to claim 3,
wherein a first member is embedded in the first connector cap part,
wherein a second member that differs from the first member is embedded in the second connector cap part at a position such that the second member faces the first member when the first connector cap part and the second connector cap part are joined together, and
wherein the first member and the second member are attracted to each other by a magnetic force.

* * * * *